United States Patent

Hardy et al.

[11] 3,970,622
[45] July 20, 1976

[54] HEAT STABILIZERS FOR POLYVINYL CHLORIDE (β-AMINO-β-ARYLACRYLONITRILES)

[75] Inventors: William Baptist Hardy, Bound Brook; Christos Savides, Piscataway, both of N.J.

[73] Assignee: American Cyanamid Company, Stamford, Conn.

[22] Filed: Nov. 24, 1975

[21] Appl. No.: 634,946

[52] U.S. Cl. .................... 260/23 XA; 260/45.9 R
[51] Int. Cl.² .................................. C08J 3/20
[58] Field of Search .............. 260/45.9 R, 23 XA

[56] References Cited
UNITED STATES PATENTS 2,850,521  9/1958  Mower .................... 260/465 D
3,723,316  3/1973  Massie .................... 260/45.9 R Primary Examiner—Hoke
Attorney, Agent, or Firm—Philip Mintz

[57] ABSTRACT

Thermal stability of vinyl chloride polymer is improved by use of a compound of the formula

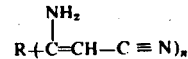

wherein $n$ is 1 or 2 and R is alkyl, alkylene, aryl, arylene, lower alkyl-substituted aryl or arylene, or fluoro-substituted aryl or arylene, alone or in combination with a divalent metal salt of a fatty acid of 12–20 carbon atoms.

12 Claims, No Drawings

HEAT STABILIZERS FOR POLYVINYL CHLORIDE (β-AMINO-β-ARYLACRYLONITRILES)

This invention relates to stabilizing vinyl chloride polymers against degradation on exposure to heat. More particularly, it relates to improving the thermal stability of vinyl chloride polymers by incorporating therein an effective amount of a certain type of β-aminoacrylonitrile.

It is well known that vinyl chloride polymers deteriorate upon exposure to elevated temperatures and that such deterioration is accompanied by progressive discoloration of the polymer generally from clear colorless to pale yellow to yellow to yellow-orange to red-orange to red to reddish brown to brown to black. It is known to inhibit such thermal degradation by the addition of stabilizers, such as those disclosed in U.S. Pat. No. 3,518,224. Illustrative of such known stabilizers are esters of β-aminocrotonic acid with 1,4-butylene glycol or octyl alcohol or thioether alcohols, such as thiodiethylene glycol or dithiotriethylene glycol. However, since all such stabilizers found to date suffer from one deficiency or another, the search continues to discover even better thermal stabilizers for vinyl chloride polymers.

In accordance with the present invention, it has been discovered that effective thermal stabilization of vinyl chloride polymers can be achieved by incorporation therein of an effective amount of a compound of the formula:

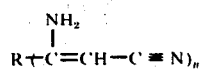

wherein $n$ is 1 or 2 and R is alkyl, alkylene, aryl, arylene, lower alkyl-substituted aryl or arylene, or fluoro-substituted aryl or arylene, alone or in admixture with a divalent metal salt of a fatty acid or mixture of fatty acids of 12–20 carbon atoms in a weight ratio of 1:2 to 2:1. Preferably, said compound is one wherein $n$ is 1 and R is phenyl, lower alkyl-substituted phenyl, fluoro-substituted phenyl, or naphthyl. Preferably said salt is calcium, barium, zinc, lead, or cadmium stearate, laurate, or oleate.

While the compounds useful for the practice of the present invention have been represented herein by the formula

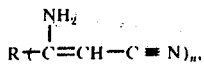

as noted above, it is to be understood that these compounds can also exist in the isomeric form

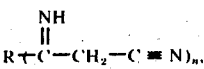

or mixtures of the two forms, and such is intended by the single formula first presented above.

Illustrative of the alkyl moieties of the foregoing compounds are such monovalent straight, branched, or cyclic alkyl groups as methyl, ethyl, n-propyl, isopropyl, n-butyl, t-butyl, cyclohexyl, octyl, lauryl, and the like having up to 12 carbon atoms. Illustrative of the alkylene moieties are such divalent straight, branched, or cyclic alkylene groups as methylene, ethylene, ethylidene, tetramethylene, 2-methyltrimethylene, cyclohexylene, hexamethylene, and the like having up to six carbon atoms. Illustrative of the aryl moieties are such monovalent aromatic groups as phenyl, naphthyl, and biphenyl. Illustrative of the arylene moieties are such divalent aromatic groups as phenylene, naphthylene, and biphenylene wherein the two points of attachment are on any two available carbon atoms thereof, whether adjacent to each other, as in o-phenylene, 1,2-naphthylene, or 2,3-biphenylene or separated from each other as in p-phenylene, 1,4-naphthylene, 1,5-naphthylene, 1,8-naphthylene, 2,4-biphenylene, 4,4'-biphenylene, 2,2'-biphenylene, etc. Illustrative of the lower alkyl moieties which may be substituted on the other carbons of the aryl or arylene moieties are such groups as methyl, ethyl, isopropyl, n-butyl, and the like having up to four carbon atoms, of which one or more may be present. Therefore, illustrative of the β-aminoacrylonitrile compounds of the above formula useful in the practice of the present invention are β-amino-β-methylacrylonitrile, β-amino-β-n-octylacrylonitrile, β-amino-β-n-dodecylacrylonitrile, β-amino-β-phenylacrylonitrile, β-amino-β-o-tolylacrylonitrile, β-amino-β-p-cumylacrylonitrile, β-amino-β-(2,4-dimethylphenyl)acrylonitrile, β-amino-β-(2-naphthyl)acrylonitrile, β-amino-β-(p-fluorophenyl)acrylonitrile, β-(3-biphenyl)acrylonitrile, β,β'-(1,2-ethylene)bis(β-aminoacrylonitrile), β,β'-(p-phenylene)bis(β-aminoacrylonitrile), β,β'(2,6-naphthylene)bis(β-aminoacrylonitrile), β,β'-(2,3-dimethyl-1,4-phenylene)bis(β-acrylonitrile, β,β'-(1,4-cyclohexylene)bis(β-aminoacrylonitrile), β,β'-(4,4'-biphenylene)-bis(β-aminoacrylonitrile), β,β'-methylenebis(β-aminoacrylonitrile), and the like.

In the practice of the present invention, it is preferred that the foregoing compounds be ones wherein the R moiety is a univalent aromatic moiety of the group phenyl, lower alkyl-substituted phenyl, fluoro-substituted phenyl, or naphthyl, such as β-amino-β-phenylacrylonitrile, β-amino-β-p-tolylphenyl, β-amino-β-(p-fluorophenyl)acrylonitrile, β-amino-β-(2-naphthyl)acrylonitrile, and the like.

In general, these compounds, useable in the practice of the present invention, can be prepared by several wellknown methods, such as by condensing the reaction product of sodium and acetonitrile with the appropriate nitrile R—C≡N$_n$ where R and $n$ are as defined above. The preparations of several of these β-aminoacrylonitrile compounds are described in R. Holtzwart, J. Praktische Chemie [2] 39, 230 (1889); E. von Meyer, J. Praktische Chemie [2] 52, 81 (1895) and [2] 78, 497 (1908); Dornow et al., Chemische Berichte 82, 254 (1949); J. Kuthan et al., Collect. Czech. Chem. Commun. 32, (12), 4309-18 (1967) and Chem. Abstracts 68, 39315K (1968); and J. Kuthan, Collect. Czech. Chem. Commun. 34 (10), 2942-51 (1969), which inter alia, discuss β-amino-β-methylacrylonitrile, β-amino-β-phenylacrylonitrile, β-amino-β-p-tolylacrylonitrile, and β-amino-β-(p-ethylphenyl)acrylonitrile.

To secure effective stabilization of the vinyl chloride polymer against thermal degradation, it is generally desirable to use these compounds in the polymer in approximately a concentration of 0.5 to 5.0% on weight of the polymer, although approximately 1.0 to 3.0% on weight of polymer is preferred. Other additives also may be present in the vinyl chloride polymer to modify it for its intended application, such as fillers, anti-static agents, lubricants, light stabilizers, pigments, dyes, plasticizers, etc. as is conventional practice.

In accordance with the present invention, vinyl chloride polymers can be stabilized against thermal degradation by use of these β-aminoacrylonitrile compounds alone or in admixture with a divalent metal salt of a fatty acid or mixture of fatty acids of 12–20 carbon atoms in a weight ratio of 1:2 to 2:1. Illustrative of the divalent metals are calcium, barium, zinc, lead, and cadmium. Illustrative of the fatty acids are lauric, oleic, and stearic acids. Representative such salts include calcium stearate, calcium laurate, calcium oleate, barium stearate, barium laurate, zinc oleate, zinc stearate, lead stearate, cadmium stearate, and the like.

These stabilizers, along with other additives, if used, are readily incorporated into the vinyl chloride polymer by such conventional processes as casting, molding, extruding, milling, mixing, and the like.

The following examples are given to illustrate the present invention. All parts are by weight unless otherwise specified.

EXAMPLE 1

To a solution of 2.0 grams (0.087 mole) of sodium in 125 milliliters of liquid ammonia was added a solution of 3.67 grams (0.089 mole) of acetonitrile in 10 milliliters of diethyl ether over a period of about five minutes. The reaction mixture was then cooled in a dry ice-acetone bath and a solution of 10.0 grams (0.065 mole) of 2-cyanonaphthalene in a minimum of dry diethyl ether was rapidly added within about five minutes after completion of the acetonitrile addition. The reaction mixture was stirred for about one and one-half hours and the ammonia was then allowed to evaporate. Water was cautiously added to the reaction mixture under nitrogen and the resulting mixture was extracted with diethyl ether. The ether was separated and the residue recrystallized from a mixture of chloroform and hexane. There was obtained 2.8 grams (22% of theoretical) of β-amino-β-(2-naphthyl)acrylonitrile, melting point 85°–90°C. Analysis: — Calculated for $C_{13}H_{10}N_2$ (percent): C, 80.39; H, 5.19; N, 14.42. Found (percent): C, 80.08; H, 4.99; N, 14.06.

EXAMPLE 2

The procedure of Example 1 was used to react 2.7 grams (0.117 mole) of sodium and 5.2 grams (0.126 mole) of acetonitrile with 10.0 grams (0.083 mole) of p-fluorobenzonitrile. After the addition of water, the reaction mixture was extracted three times with chloroform. The combined chloroform extracts were concentrated to obtain a dark-colored crystalline mass which was recrystallized four times from a mixture of chloroform and hexane to obtain yellow plates of β-amino-β-(p-fluorophenyl)acrylonitrile, mleting point 110°–112°C. Analysis: — Calculated for $C_9H_7N_2F$ (percent): C, 66.66; H, 4.35; N, 17.27; F, 11.72. Found (percent): C, 66.48; H, 4.34; N, 17.21; F, 11.19.

EXAMPLE 3

To a 16.7% solution of Geon 103EP polyvinyl chloride in tetrahydrofuran was added an amount of stabilizer to provide 3% by weight of stabilizer on weight of polyvinyl chloride and a film was cast therefrom and dried. The film was then exposed to heat at 193.3°C. (380°F.) in a press under a pressure of fifteen tons for twenty minutes, after which the films were observed for discoloration. As noted above, thermal degradation of polyvinyl chloride is accompanied by progressive discoloration of the polymer from clear colorless through various stages to black. Table I shows the results of tests with four stabilizers of the present invention and a control film similarly made and tested but without stabilizer.

Table 1

| Stabilizer | Color of film 20 mins. at 380°F. |
|---|---|
| β-amino-β-phenylacrylonitrile | almost colorless |
| β-amino-β-(p-tolyl)acrylonitrile | almost colorless |
| β-amino-β-(2-naphthyl)acrylonitrile | pale yellow |
| β-amino-β-(p-fluorophenyl)acrylonitrile | pale yellow |
| control - no stabilizer | reddish brown |

EXAMPLE 4

The procedure of Example 3 was used to test various mixtures of β-amino-β-phenylacrylonitrile and calcium stearate at a total concentration of 3% on weight of polyvinyl chloride. However, in this test, the heat treatment under pressure lasted for thirty minutes prior to observation of the films. Table II shows the results of this series of tests which show the efficacy of approximately equal weight mixtures of the two additives for thermal stabilization.

Table II

| Mixture Proportion | Color of film 30 mins. at 380°F. |
|---|---|
| (parts β-amino-β-phenylacrylonitrile to parts calcium stearate) | |
| 1 to 1 | almost colorless |
| control - no additives | red-brown with black spots |

We claim:

1. A composition comprising a vinyl chloride polymer containing an amount, effective to improve the thermal stability of said polymer, of a compound of the formula:

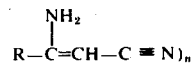

wherein n is 1 or 2 and R is alkyl, alkylene, aryl, arylene, lower alkyl-substituted aryl or arylene, or fluoro-substituted aryl or arylene.

2. A composition as defined in claim 1 additionally containing a divalent metal salt of a fatty acid or mixture of fatty acids of 12–20 carbon atoms, the weight ratio of said salt to said compound being between 1:2 and 2:1.

3. A composition as defined in claim 1 wherein said amount is 0.5 to 5.0 percent on weight of said polymer.

4. A composition as defined in claim 1 wherein, in said compound, n is 1 R is phenyl, lower alkyl-substituted phenyl, fluoro-substituted phenyl, or naphthyl.

5. A composition as defined in claim 4 additionally containing a divalent metal salt of a fatty acid or mixture of fatty acids of 12–20 carbon atoms, the weight ratio of said salt to said compound being between 1:2 and 2:1.

6. A composition as defined in claim 5 wherein said salt is calcium, barium, zinc, lead, or cadmium stearate, laurate, or oleate.

7. A composition as defined in claim 4 wherein the amount of said compound is 0.5 to 5.0 percent on weight of said polymer.

8. A composition as defined in claim 1 wherein said compound is β-amino-β-phenylacrylonitrile.

9. A composition as defined in claim 1 wherein said compound is β-amino-β-p-(lower alkylphenyl)acrylontrile.

10. A composition as defined in claim 9 wherein said compound is β-amino-β-p-tolylacrylonitrile.

11. A composition as defined in claim 1 wherein said compound is β-amino-β-(2-naphthyl)acrylontirile.

12. A composition as defined in claim 1 wherein said compound is β-amino-β-(p-fluorophenyl)acrylontrile.

* * * * *